(12) United States Patent
Helfenbein et al.

(10) Patent No.: US 9,377,775 B2
(45) Date of Patent: Jun. 28, 2016

(54) METHOD AND DEVICE FOR PROGRAMMING A CORDLESS HANDPIECE FOR ROOT CANAL TREATMENT

(71) Applicant: W&H Dentalwerk Bürmoos GmbH, Bürmoos (AT)

(72) Inventors: Gerald Helfenbein, Gilgenberg (AT); Stefan Putz, Oberndorf bei Salzburg (AT); Rainer Schröck, Bürmoos (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 14/577,577

(22) Filed: Dec. 19, 2014

(65) Prior Publication Data
US 2015/0105916 A1   Apr. 16, 2015

Related U.S. Application Data

(63) Continuation of application No. 12/646,576, filed on Dec. 23, 2009, now Pat. No. 8,936,465.

(30) Foreign Application Priority Data

Dec. 24, 2008   (EP) .................................. 08022455

(51) Int. Cl.
*G05B 19/4093* (2006.01)
*G05B 19/18* (2006.01)
*A61C 5/02* (2006.01)

(52) U.S. Cl.
CPC ............ *G05B 19/40938* (2013.01); *A61C 5/02* (2013.01); *G05B 19/182* (2013.01); *G05B 2219/45167* (2013.01)

(58) Field of Classification Search
CPC ........... G05B 19/40938; G05B 19/182; G05B 2219/45167; A61C 5/02
See application file for complete search history.

(56) References Cited

U.S. PATENT DOCUMENTS

| 4,180,812 A | 12/1979 | Kaltenbach et al. |
| 5,295,833 A | 3/1994 | Chihiro et al. |

(Continued)

FOREIGN PATENT DOCUMENTS

| DE | 195 20 765 A1 | 12/1995 |
| DE | 195 20 765 B4 | 7/2004 |

(Continued)

OTHER PUBLICATIONS

European Search Report for EP08022455 (mailed May 25, 2009).

(Continued)

*Primary Examiner* — Zachary K Huson
*Assistant Examiner* — Ronald Modo
(74) *Attorney, Agent, or Firm* — Klarquist Sparkman, LLP

(57) ABSTRACT

A method and device for programming a cordless handpiece used for root canal treatment and having a first memory and a tool holder for a treatment tool are described. The method includes providing a first data volume having a plurality of data sets in a second memory separate from the first memory, each of the data sets comprising at least one parameter assigned to the cordless handpiece and/or to the treatment tool, selecting at least some of the data sets from the first data volume in the second memory, transmitting the selected data sets from the second memory to the first memory of the handpiece, and selecting a data set from the updated first memory for operation of the handpiece.

25 Claims, 1 Drawing Sheet

(56) References Cited

U.S. PATENT DOCUMENTS

| | | | |
|---|---|---|---|
| 7,965,851 B2 | 6/2011 | Bengtsson | |
| 2003/0069673 A1* | 4/2003 | Hong et al. | 701/29 |
| 2003/0195642 A1* | 10/2003 | Ragnini | 700/56 |
| 2005/0042572 A1 | 2/2005 | Katsuda et al. | |
| 2008/0170130 A1* | 7/2008 | Ollila et al. | 348/211.99 |
| 2008/0254404 A1* | 10/2008 | Heraud | 433/27 |
| 2008/0293008 A1* | 11/2008 | Regere | A61C 1/0015 433/119 |
| 2009/0172279 A1* | 7/2009 | Yuan et al. | 711/115 |
| 2009/0271016 A1 | 10/2009 | Wampler et al. | |

FOREIGN PATENT DOCUMENTS

| | | |
|---|---|---|
| DE | 10 2007 020100 | 10/2008 |
| EP | 788778 | 8/1997 |
| EP | 1172071 | 1/2002 |
| JP | 08000640 | 1/1996 |
| JP | 2003159262 | 6/2003 |
| JP | 2006334416 | 12/2006 |

OTHER PUBLICATIONS

Office Action from Japanese Patent Office for JP2009290327 (mailed Oct. 8, 2013).

* cited by examiner

METHOD AND DEVICE FOR PROGRAMMING A CORDLESS HANDPIECE FOR ROOT CANAL TREATMENT

CROSS REFERENCE TO RELATED APPLICATIONS

The present application is a continuation of U.S. patent application Ser. No. 12/646,576, filed Dec. 23, 2009, which claims priority from European Patent Application No. 08022455 filed Dec. 24, 2008, now European Patent No. 2201907, both of which are incorporated herein by reference.

BACKGROUND

1. Field

This application relates to a method and a device for programming a cordless medical or dental handpiece for root canal treatment.

2. Description of Prior Art

Conventional cordless devices for root canal treatment have at least one cordless handpiece and a charger. The cordless handpiece is equipped with a drive motor and a battery for supplying power to the motor, in addition to a tool holder for a treatment tool. A measurement circuit for measuring the root canal length and/or the load applied to the tool is preferably also provided in the handpiece. In measuring the root canal length, the treatment tool retained in a tool holder is used as an electrode and is electrically connected to the root canal length measuring circuit via a contact piece provided in the head of the handpiece or externally on the handpiece. If the control arrangement of the measurement circuit indicates that the tool has reached a target position in a root canal or that a predefined torque has been exceeded, it automatically stops the tool or automatically rotates it in the opposite direction. Because of the anatomy of the root canal to be treated, a plurality of different tools, in particular files of different diameters and tool properties, e.g., breaking strengths, must be used to prepare a root canal. These tools thus differ significantly with regard to their parameters to be set, e.g., the maximum allowed rotational speed or torque.

Such a medical or dental device, and the method for adjusting the cordless handpiece with the parameters of the treatment tool for root canal treatment are known from DE 19520765 B4.

The device for root canal treatment known from the prior art having at least one cordless handpiece and one charger has a plurality of adjusting elements for adjusting the handpiece to the respective parameters of the tool being used. The different adjusting elements, in particular for adjusting the rotational speed, the maximum allowed torque and the autofunction parameters, e.g., autostop or autoreverse, may be provided on both the cordless handpiece and the charger. The user may thus adjust his handpiece to the parameters of the tool being used by means of the plurality of adjusting elements.

One disadvantage of this prior art approach has proven to be the manual adjustment of the individual tool and handpiece parameters by means of the plurality of adjusting elements on the handpiece or on the charger.

Operation of the cordless device for root canal treatment is complex and time-consuming due to the numerous tool parameters, e.g., the maximum rotational speed, the maximum torque or the numerous handpiece parameters, e.g., the autofunction parameters (such as autostop or autoreverse, in which the tool automatically rotates in the opposite direction or stops when the tool has reached a certain position in the root canal or when a certain load is applied to the tool). Due to the number of parameters, each time a tool is changed, the user must adjust the handpiece to comply with the new tool and handpiece parameters. To do so, the user must operate the numerous adjusting elements on the handpiece and/or on the charger.

In addition, the device known in the prior art for root canal treatment entails the risk of possible error sources. Due to the numerous parameters to be adjusted, there is the risk that the user might set possible values incorrectly, resulting in complications in treatment of the root canal, e.g., breakage of the file in the root canal because the torque limits for the tool being used are set too high.

SUMMARY

Described below are embodiments of a method and a device for programming a cordless handpiece for root canal treatment that will make it possible to avoid or at least reduce the disadvantages of the prior art, and to program a cordless handpiece easily and with the exclusion of possible error sources.

According to one exemplary embodiment of a method for programming a cordless handpiece used for root canal treatment, having a first memory and a tool holder for a treatment tool, the handpiece is programmed by providing a first data volume having a plurality of data sets in a second memory, each of the data sets comprising at least one parameter assigned to the cordless handpiece and/or the treatment tool to be operated, selecting at least some of the data sets from the first data volume in the second memory, transmitting the selected data sets from the second memory to the first memory of the handpiece and selecting, manually or automatically, a data set from the updated first memory for operation of the handpiece.

The second memory is separate from the first memory of the handpiece. The second memory may be in a base station (which can be designed as a charger for the battery operated handpiece), or configured as a separate memory element.

Each of the data sets may comprise at least one tool parameter for a tool, such as for a dental file used to treat a root canal, and/or a handpiece parameter. A designation, such as a name of each respective file, can be assigned to each data set. The user can preselect one or more desired files, for example, the files commonly used by the user, from a library provided in the second memory, which may contain, e.g., all of the data sets, such as data sets of all the files available on the market. The user may then make his preselection of data sets from the library, such as by using at least one control element, to which end he selects the data sets according to which files are desired, which may be which files he uses especially often or which files he needs for the next treatment. Then, a data volume, which may be a partial data volume comprising at least one data set, or a total data volume, is transferred to the memory of the handpiece. This is done by establishing a connection between the handpiece with the first memory and the second memory, or by connecting only the first memory itself. The first memory may be configured as a memory card having contacts, or as any other suitable memory element. Then, e.g., using at least one control element, the user can select the appropriate data set, e.g., the name of the file, which is used.

The at least one control element for selection of the partial data volume or a data set can be configured as a pushbutton, potentiometer, joystick, proximity sensor, touchscreen display or other element for selecting from among a plurality of parameters. In one embodiment, the at least one control element preferably has multiple functions for menu guidance in the file library, e.g., "left," "right," "up" and "down" functions as well as an actuation function, such as "ok." In addition, further control elements may be provided on the handpiece or on the base station for parameters including both the tool and the handpiece, e.g., an on/off switch for the root canal length measurement circuit or a torque reducing switch for difficult anatomy, reducing all set torques by 5% to 20%.

To ensure a complete first data volume for all the files available on the market, the first data volume must be updated regularly to include all new files and their parameters as a data set. This is made possible by transmission of the existing data sets and the new data sets, or only the new data sets, from a third memory to the second memory. To do so, the third memory, which can be configured as a memory card, USB stick, Smart Media card, memory stick, multimedia card or Secure Digital memory card (SD card or mini-SD card), is connected to the second memory via a suitable interface and the data sets are transmitted. In another embodiment, data may also be transmitted by wireless data transmission (e.g., via radiofrequency, infrared, inductive or capacitive data transmissions) from the third memory to the second memory.

As an alternative to storage of the first data volume in a second memory, such as in a base station, the first data volume may also remain in the third memory, which thus serves to update the first data volume. The handpiece is thus programmed directly by transmission of the appropriate data sets from the third memory, in particular from a memory card. The total data volume then remains in the third memory.

Selection of the partial data volume, i.e., of one or more of the data sets, is made by at least one control element, which is arranged on or connected to the handpiece itself, the second memory or the third memory. The user thus programs his handpiece with only the data sets relevant for him.

The selection of a data set from the updated first memory may be made manually by the user via at least on control element or automatically. Automatic selection can be accomplished with a tool identification circuit, which may use one or more of: radiofrequency waves (RFID), a barcode on the tool and a reader on the handpiece, at least one sensor on the handpiece and identification on the basis of a magnetic field generated, and determination of the tool material, the material thickness or the material hardness. In this embodiment, the user need only make a preselection of the dental tools (i.e., files in this example) available for use. All additional steps in programming the handpiece are then performed automatically.

The present method and device for programming a cordless handpiece provide a number of significant advantages. Rapid and simple operation for the user is ensured by providing a first data volume having a plurality of data sets appropriate for each tool and handpiece that may be used. It is no longer necessary to manually set each parameter for the tool and/or the handpiece before operation of each operation tool on the handpiece or on a base station. This yields time savings for the user in programming the presettings of the tool and the handpiece as well as minimizing the control elements for adjusting the various parameters.

In addition, possible error sources are at least minimized if not entirely prevented by the present method and device on the basis of finished data sets and data sets coordinated with the tool and handpiece. Through manual or automatic selection of finished data sets on the handpiece, it is impossible for the user to set wrong parameters for a tool, e.g., the maximum allowed rotational speed or torque.

Another advantage is the possibility of selecting a partial data volume from a first data volume for programming the handpiece. A comprehensive preselection on the handpiece is ensured by transmitting just a partial data volume, in particular the data sets of the files being used by the user. In addition, a complete data volume is available to the user for preferably all the files obtainable on the market.

The first data volume in the second memory is guaranteed to be up-to-date by another memory, in particular a memory card. By loading the second memory by means of an additional memory, the data volume may be updated and completed constantly with new data sets.

Within the scope of this application, it is understandable that the present method and device for programming a handpiece are not limited to the handpieces for root canal treatment specified in the description. Instead, additional handpieces may be programmed for general treatment in the medical field, in particular in the dental field.

These and other embodiments are explained in greater detail below on the basis of exemplary embodiments and in conjunction with the accompanying drawings.

DETAILED DESCRIPTION

Figure 1:
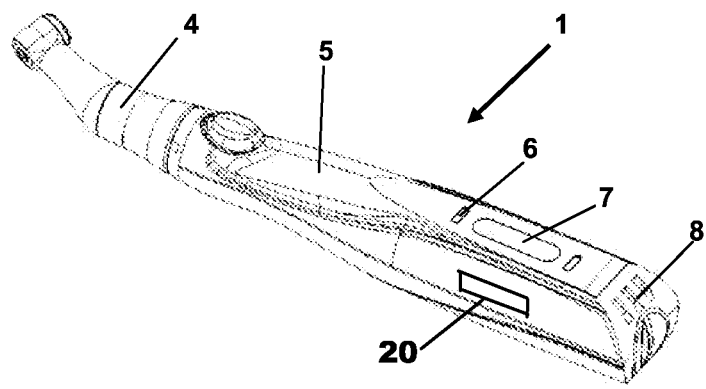
FIG. 1 shows a cordless handpiece for root canal treatment having a first memory comprising an instrument part and a main part.

FIG. 1 shows a cordless handpiece 1, preferably for root canal treatment. The handpiece 1 consists of an instrument part 4 and a main part 5. The main part 5 forms the drive unit for the cordless handpiece 1. In addition to the drive motor with an output shaft for coupling the instrument part 4, a battery (not shown), which is used to supply electric power to the motor, is provided in the handpiece. For charging the battery, charging contacts 8 are provided on the main part 5. In addition, a control and a first memory 20 are arranged in the main part 5 for storing a partial data volume transmissible to the handpiece 1. A data set is selected from the partial data volume by at least one control element 6 and a display 7. The handpiece also has a data receiving unit for transmitting a partial data volume from the base station 2 or from an additional memory 3 to the handpiece 1. This interface is preferably designed as a wired interface via the charging contacts 8 or via additional electric contacts (not shown). The instrument part 4 serves to transmit the drive movement from the output shaft of the drive motor to the tool.

Figure 2:
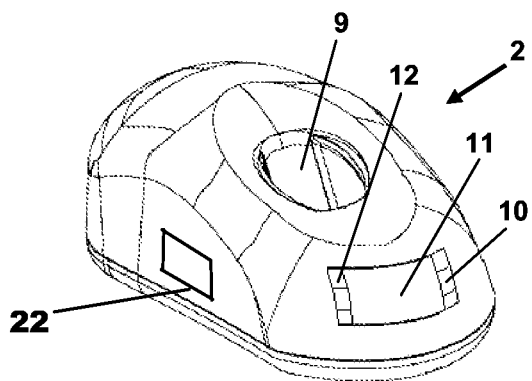
FIG. 2 shows a base station having a second memory for receiving the cordless handpiece, in particular for supplying power to the handpiece.

FIG. 2 shows a base station 2 corresponding to the cordless handpiece 1. The base station 2 is preferably designed as a charger for the cordless handpiece 1. A charging circuit for charging the battery in the handpiece 1 is provided in the base station 2. To this end, the handpiece 1 is connected to the base station 2, e.g., by inserting the handpiece 1 in a receptacle 9. In addition, a control and a second memory 22 are also provided on the base station 2. This second memory 22 serves to provide the first data volume. By means of the at least one control element 10 as well as the display 11 on the base station, the user may select a partial data volume to be transmitted to the handpiece 1. In addition to the control element 10, other control elements 12 may also be arranged on the base station 2 for setting additional functions of the tool and handpiece. For transmission of a partial data volume from an external memory, such as a third memory 3 (described below) to the base station 2 (second memory 22), and from the base station 2 (second memory 22) to the handpiece, the base station 2 has a data receiving and transmitting unit (not shown). The base station 2 can include an interface between the third memory 3 and the base station 2, such as one configured for a wired connection, in particular a receptacle for a memory card, a port for a standardized or proprietary connector (e.g., a USB port) or another form of physical interface providing a wired connection.

Figure 3:
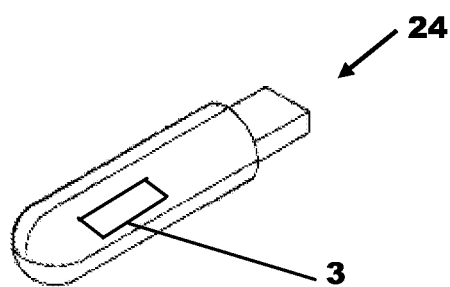
FIG. 3 shows an additional memory for loading the memory in the base station and/or the memory in the handpiece.

FIG. 3 shows an example of the third memory 3, which as illustrated is embodied as a portable memory element 24 (e.g., a USB stick). Alternatively, the third memory 3 could be embodied as, e.g., a Smart Media card, memory stick, multimedia card or Secure Digital memory card (SD card or mini-SD card). The third memory 3 serves to transmit data sets to the base station 2 or directly to the handpiece 1, if the handpiece is provided with a suitable interface for connection to the third memory 3.

For embodiments in which there is no second memory in the base station, the second memory can be embodied as a portable memory element (such as shown in FIG. 3).

This application is not limited to the exemplary embodiments described herein. Within the scope of the invention, it is of course self-evident that data may be transmitted from the base station 2 to the handpiece 1 or from the additional, in particular third, memory 3 to the base station 2 or directly to the handpiece 1 by wireless data transmission. To this end, the transmission is preferably accomplished by means of radiofrequency waves, infrared, wireless or inductive or capacitive data transmission.

What is claimed is:

1. A method for programming a cordless medical or dental handpiece having a first memory and a tool holder for a treatment tool, comprising:
   providing a plurality of data sets in a portable memory element comprising a second memory separate from the first memory, each of the data sets in the second memory comprising at least one parameter assigned to the cordless handpiece and/or to the treatment tool;
   connecting the portable memory element to the handpiece;
   selecting at least one of the data sets in the second memory using the handpiece or the portable memory element (1) manually by actuating at least one control element on the handpiece or on the portable memory element or (2) with automatic tool identification on the handpiece or on the portable memory element;
   varying the selected at least one data set with at least one control element on the handpiece or on the portable memory element; and
   transmitting the selected and varied at least one data set from the portable memory element to the first memory of the handpiece to update the first memory, thereby allowing operation of the handpiece according to the selected and varied at least one data set in the updated first memory.

2. The method according to claim 1, wherein the at least one data set is transmitted from the portable memory dement to the first memory of the handpiece by a wired connection or wirelessly.

3. The method according to claim 1, wherein selecting at least one of the data sets in the second memory is achieved by selecting a name of a file.

4. The method according to claim 1, wherein the second memory of the portable memory element is updatable with data sets from a third memory.

5. The method according to claim 4, wherein the second memory is updatable with data sets from a third memory by one of a wired connection between the second memory and the third memory and a wireless connection between the second memory and the third memory.

6. The method according to claim 1, wherein at least one of the first memory and the second memory comprises a memory card.

7. The method according to claim 1, wherein at least one of the data sets comprises at least one of a tool rotational speed, a tool torque and a tool name associated with a respective tool.

8. The method according to claim 1, wherein the at least one parameter of the data sets in the second memory assigned to the cordless handpiece comprises at least one autofunction parameter selected from a group comprising autoreverse, autostop and autoforward parameters.

9. The method according to claim 1, further comprising selecting the at least one data set from the updated first memory of the handpiece by manually selecting the at least one data set from the updated first memory using a handpiece control element.

10. The method according to claim 1, further comprising selecting the at least one data set from the updated first memory of the handpiece by selecting the at least one data set with automatic tool identification using at least one of radiofrequency waves, RFID, barcode scanning and at least one sensor.

11. The method according to claim 1, wherein varying the selected at least one data set comprises varying or reducing a torque value of the selected at least one data set.

12. A cordless medical or dental handpiece assembly, comprising:
    a cordless handpiece having a first memory and a tool holder for a treatment tool; and
    a portable memory element for programming the cordless handpiece, the portable memory element having a second memory separate from the first memory of the handpiece, the second memory comprising a plurality of data sets, each of the data sets comprising at least one parameter assigned to the cordless handpiece and/or the treatment tool,
    the handpiece or the portable memory element comprising at least one of a selecting control element manually operable to select at least one data set from the second memory or an automatic tool identification circuit operable to identify an installed treatment tool installed in the holder and to select the at least one data set based on the installed treatment tool,
    the handpiece or the portable memory element further comprising a vary control element operable to vary the selected at least one data set, and
    a transmission device which is operable to transmit the selected and varied at least one data set from the portable memory element to the first memory of the handpiece to update the first memory, thereby allowing operation of the handpiece according to the at least one data set in the updated first memory.

13. The assembly according to claim 12, wherein the transmission device comprises one of electrical contacts for establishing a wired connection and a wireless connection for transmitting the selected and varied at least one data set to the first memory.

14. The assembly according to claim 12, wherein the portable memory element is connectable with a third memory, and wherein the third memory is operable to update the second memory in the portable memory element with multiple updated data sets.

15. The assembly according to claim 12, wherein the varying control element is operable to vary or reduce a torque value of the selected at least one data set.

16. The assembly according to claim 12, wherein the control element on the handpiece or the automatic tool identification is operable to select at least one data set from the second memory through selecting a name of a file.

17. A method for programming a cordless medical or dental handpiece having a first memory and a tool holder for a treatment tool, comprising:
  providing a plurality of data sets in a portable memory element having a second memory separate from the first memory of the handpiece, each of the data sets in the second memory comprising at least one parameter assigned to the cordless handpiece and/or to the treatment tool;
  connecting the portable memory element to the handpiece;
  selecting at least one of the data sets in the second memory using the handpiece manually by actuating at least one control element arranged on the handpiece; and
  transmitting the selected at least one data set from the second memory of the portable memory element to the first memory of the handpiece to update the first memory, thereby allowing operation of the handpiece according to the at least one data set in the updated first memory.

18. The method according to claim 17, further comprising selecting the at least one data set from the updated first memory of the handpiece (1) by manually selecting the at least one data set from the updated first memory using a handpiece control element or (2) by selecting the at least one data set with automatic tool identification using at least one of radiofrequency waves, RFID, barcode scanning and at least one sensor.

19. The method according to claim 17, further comprising selecting at least one of the data sets in the second memory using an automatic tool identification on the handpiece.

20. The method according to claim 17, wherein selecting at least one of the data sets in the second memory is achieved by selecting a name of a file.

21. The method according to claim 17, further comprising displaying the selected at least one data set on a display coupled to the portable memory element.

22. A cordless medical or dental handpiece assembly, comprising:
  a cordless handpiece having a first memory, a tool holder for a treatment tool, and a control element for selecting a data set; and
  a portable memory element used to program the cordless handpiece, the portable memory element having a second memory separate from the first memory of the handpiece, the second memory comprising a plurality of data sets, each of the data sets comprising at least one parameter assigned to the cordless handpiece and/or a selected treatment tool,
  wherein the control element on the handpiece is manually operable to select at least one data set from the second memory, and
  wherein the at least one data set selected through the control element on the handpiece is transmitted through a transmission device from the second memory of the portable memory element to the first memory of the handpiece to update the first memory, thereby allowing operation of the handpiece according to the at least one data set in the updated first memory.

23. The assembly according to claim 22, wherein the transmission device comprises electrical contacts for establishing a wired connection for transmitting the selected at least one data set to the first memory via the wired connection or is operable to cause the selected at least one data set to be transmitted wirelessly to the first memory.

24. The assembly according to claim 22, wherein the control element on the handpiece is manually operable to select at least one data set from the second memory through selecting a name of a file.

25. The assembly according to claim 22, wherein the portable memory element comprises a display which is configured to display the selected at least one data set.

* * * * *